United States Patent [19]

Hager

[11] Patent Number: 4,903,694

[45] Date of Patent: Feb. 27, 1990

[54] VENTILATING APPARATUS FOR A PROTECTIVE SUIT

[75] Inventor: Volker Hager, Vienna, Austria

[73] Assignee: J. Blaschke Pumpen-Filteranlagen, Vienna, Austria

[21] Appl. No.: 321,280

[22] Filed: Mar. 9, 1989

[30] Foreign Application Priority Data

Mar. 9, 1988 [AT] Austria .................................. 623/88
Jan. 16, 1989 [AT] Austria .................................. 75/89

[51] Int. Cl.[4] .............................................. A61M 16/00

[52] U.S. Cl. .......................... 128/204.15; 128/201.25; 137/625.23; 137/863; 251/298; 251/340

[58] Field of Search ...................... 128/204.15, 201.25, 128/201.28, 204.18, 204.21, 205.12, 205.24, 205.26, 205.27, 206.15, 207.16; 137/596, 596.12, 625.23, 625.25, 625.48, 625.46, 625.21, 597, 862, 863; 251/298, 205, 208, 340

[56] References Cited

U.S. PATENT DOCUMENTS 2,819,590 1/1958 Green ............................ 128/204.15
2,824,557 2/1958 Mejean et al. ................. 128/201.28
3,049,896 8/1962 Webb ............................. 128/201.25
3,496,703 2/1970 MacLeod et al. .............. 128/204.15
4,478,216 10/1984 Dukowski ...................... 128/205.12
4,522,639 6/1985 Ansite et al. ................... 128/201.25
4,705,073 11/1987 Beck .............................. 128/205.24

FOREIGN PATENT DOCUMENTS 0146161 6/1985 European Pat. Off. ....... 128/205.27
2421297 11/1974 Fed. Rep. of Germany ....................... 128/205.12
0782137 3/1935 France ........................... 128/205.12
2546292 11/1984 France ........................... 128/204.18
2058577 4/1981 United Kingdom ........... 128/201.25

*Primary Examiner*—Eugene H. Eickholt
*Attorney, Agent, or Firm*—Herbert Dubno

[57] ABSTRACT

The ventilating apparatus for a protective suit has a portable, comparatively small housing in which a blower driven by a battery-powered electric motor is mounted. The high pressure side of the blower is provided with a plurality of different connectors which provide different flow rates. The flow rate through the connectors can be made changable by a rotary slide valve which comprises a flexible plate and a handle for exterior operation. A connector on the high pressure side can be provided to supply air to a breathing mask as well as to ventilate the suit. Because a significantly reduced air flow rate is necessary for the breathing mask an orifice plate or diaphram is provided for the connector for the breathing mask. The vacuum or low pressure side of the blower may be provided with a filter connector.

9 Claims, 1 Drawing Sheet

VENTILATING APPARATUS FOR A PROTECTIVE SUIT

FIELD OF THE INVENTION

My present invention relates to a ventilating apparatus for a protective suit.

BACKGROUND OF THE INVENTION

A protective suit used in an area contaminated with a toxic agent must be air-tight and gas tight.

The wearer can remain in the suit only a certain limited time. To extend that time a ventilation apparatus for the suit is known having a mechanism which is lightweight so that it is extremely easy to carry and which supplies sufficient air flow at sufficient pressure.

In an especially advantageous ventilation apparatus the blower is a radial blower. Only a comparatively small radial blower is needed to provide sufficient air flow through or into the protective suit. It can be easily carried by the protective suit wearer.

OBJECTS OF THE INVENTION

The primary purpose of my present invention is to improve the known apparatus so that in addition to being used to ventilate the protective suit it can be used to supply air to a breathing mask. It is however not enough just to provide additional connectors. It has been found that the required air flow rates for ventilating the protective suit on the one hand and for supplying air to the breathing mask on the other hand are quite different. A ratio of flow rates of 1:4 to 1:6 is typical.

It is another object of my invention to provide an improved ventilating apparatus for a protective suit which has at least two connectors on the high pressure side of the blower which easily and simply supply air at different flow rates.

SUMMARY OF THE INVENTION

These objects and others which will become more readily apparent hereinafter is attained in accordance with my invention in a ventilating apparatus for ventilation of a protective suit, in which a blower driven by an electric motor is mounted in a portable housing.

According to my invention a plurality of connectors having differing throughput flow rates are provided on the high pressure side of the blower.

According to a feature of the invention the connectors can have different throughput flow cross sections. These different flow cross sections can be provided by different-size orifices formed by an orifice plate or by diaphragms.

To provide a unit which can be adjusted to different conditions in an easy way in a particularly advantageous embodiment of my invention at least one of the connectors on the high pressure side is provided with a control device for changing the throughput flow rate. This control device can be a rotary slide valve, which has a valve disk on the inside of the housing slidable over the openings of the connectors by a handle operable from the outside.

If at least two connectors are located in the rotation range of the rotary slide valve disk a additional degree of regulation results. Thus both connectors can be controlled by the one rotary slide valve.

It is also advantageous when the rotary slide valve disk is made from a flexible plate. In such an embodiment the inside of the connector and/or of the housing does not need to be configured in a special way for sealing and no special guide for the rotary slide valve disk is required, because the flexible plate is pressed by the air flow from the blower on the wall containing the openings of the connectors.

So that no heating of the forced-in air can occur in a metallic housing, e.g. in strong solar radiation, the housing or housing of the unit is provided with a thermal insulation layer at least in the vicinity of the blower.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
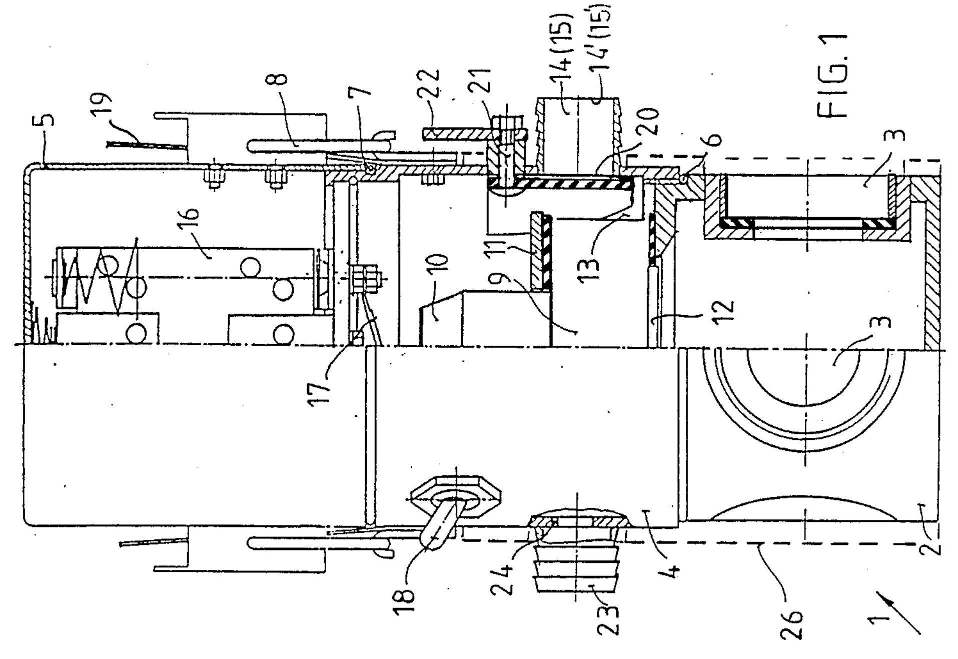
FIG. 1 is partially a side elevational view (left side), partially a longitudinal cross sectional view (right side) of a ventilating apparatus according to my invention.
Figure 2:
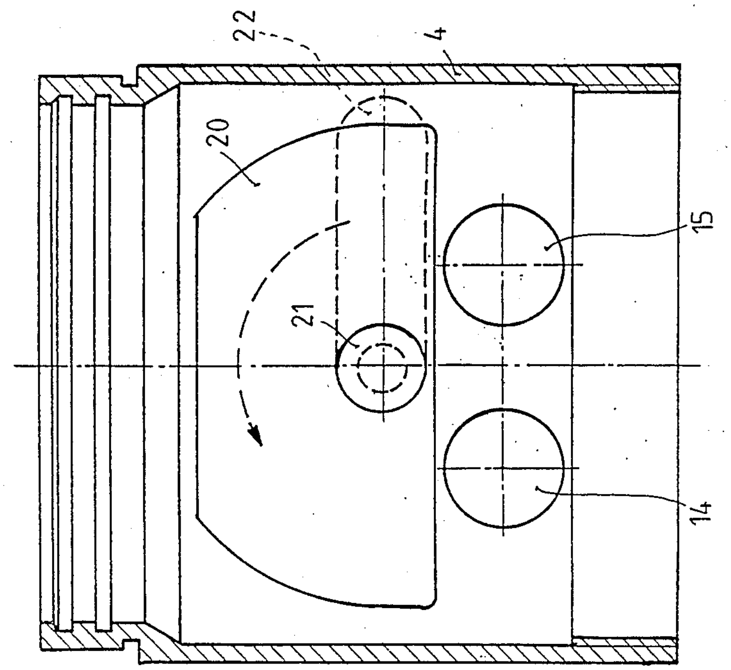
FIG. 2 is a detailed cross sectional view through the housing portion of the ventilating apparatus with a rotary slide valve according to my invention.

The portable, comparatively small housing 1 which houses the ventilation unit according to my invention has a lower portion 2 with two inset filter connectors 3, a central portion 4 and a cover 5.

The central portion 4 is screwed together or coupled with the lower portion 2 with an intervening seal 6 and the cover 5 is held by rapid closure 8 on the central portion, similarly with a seal 7 interposed.

A carry belt 19 is attached adjacent the central portion 4 in the vicinity of the rapid closure 8. A radial blower 9 with an electric motor 10 is mounted on the lower portion 2 by a disk 11 using screws (not shown) so that the low pressure or vacuum side 12 of the blower 9 is open toward and communicates with the filter connectors 3. Connectors 14 and 15 to which connecting tubes for the protective suit and/or for the breathing mask can be connected are located in the central portion 4 in the vicinity of the high pressure side 13 of the blower 9.

Batteries 16, from which 17 leads extend which connect to a switch 18 and/or the blower electric motor 10, are accommodated in the upper portion of the housing 1, in the vicinity of the cover 5.

A rotary slide valve comprising a rotary slide valve disk, i.e. flexible plate 20, is provided adjacent both connectors 14 and 15. The rotary slide valve is rotatable by a handle 22 connected with the plate 20 by a shaft 21 mounted on the outside of the central portion 4.

The plate 20 can be partially or completely placed over one of the openings 14' or 15' and/or over both openings 14', 15' of the connectors 14, 15 so that a very large control range is provided and thus the ventilation unit can be adjusted to fit a wide variety of conditions.

Because of the flexibility of the plate 20 it is pressed by the pressure produced by the blower 9 on the edges of the openings 14', 15' of the connectors 14, 15 and it is not required to provide a special guide for the plate 20 or to suitably configure the surfaces which cooperate.

In FIG. 1 moreover a special connector 23 whose throughput cross section is reduced by an orifice plate 24 is illustrated in FIG. 1. A throttle is provided by this orifice plate 24 so that a smaller flow rate of air through the connector 23 than through the connectors 14 and/or 15 occurs with the rotary slide valve open or not present.

A breathing mask can be connected to the connector 23, which likewise requires a smaller flow of air than a protective suit. It is thus possible to provide a ventilation unit according to my invention with only the connector 14 (without rotary slide valve) and the connector 23. Also different flow rates can be provided at both of these connectors.

So that the air drawn in by the housing is not heated, e.g. by solar radiation, the housing, especially the lower portion 2 and the central portion 4, can be provided with a thermal insulation layer. Such layer 26 attached to the exterior is indicated by the dashed lines. The layer can be also provided on the inside of the unit.

It is also possible to provide the blower 9 with two spiral-shaped housings enclosing different peripheral portions. According to the degree to which the spiral housings extend around the blower housing different flow rates can be set for the respective connector pipe of the housing.

I claim:

1. In a ventilating apparatus for ventilation of a protective suit comprising a blower driven by an electric motor mounted in a portable housing, said blower having a vacuum side and a high pressure side, and a connector for connection to said protective suit on said high pressure side of said blower, the improvement comprising a plurality of said connectors on said high pressure side of said blower having different flow rates.

2. The improvement defined in claim 1 wherein said connectors have different throughput cross sections.

3. The improvement defined in claim 1 further comprising a control device for changing said flow rate for at least one of said connectors on said high pressure side of said blower and an opening in said housing for each of said connectors.

4. The improvement defined in claim 3 wherein said control device comprises a rotary slide valve disk inside said housing which is slidable over said openings of said connectors by an exteriorly manually-operated handle.

5. The improvement defined in claim 4 wherein at least two of said connectors are located in the rotary range of said rotary slide valve disk.

6. The improvement defined in claim 4 wherein said rotary slide valve disk comprises a flexible plate.

7. The improvement defined in claim 1 further comprising a thermally insulating layer provided on said housing at least in the vicinity of said blower.

8. A ventilating apparatus for ventilation of a protective suit comprising:

a portable housing with a thermally insulating layer;

a blower driven by an electrical motor mounted in said portable housing, said blower having a vacuum side and a high pressure side;

a plurality of connectors on said high pressure side of said blower including one for connection to said protective suit, said connectors providing a plurality of different flow rates and each having an opening inside said housing; and a control device comprising a rotary slide valve disk made of a flexible plate positioned adjacent said openings of said connectors inside said housing, said rotary slide valve disk being slidable over said openings of said connectors by operation of an exterior manually-operated handle.

9. A ventilating apparatus according to claim 8 further comprising a filter connector on said vacuum side of said blower.

* * * * *